United States Patent [19]

Wells

[11] Patent Number: 5,282,982
[45] Date of Patent: Feb. 1, 1994

[54] BLOOD WASHING METHOD

[76] Inventor: John R. Wells, 4372 Keystone Ave., Culver City, Calif. 90024

[21] Appl. No.: 729,076

[22] Filed: Jul. 12, 1991

[51] Int. Cl.$^5$ .............................................. B01D 21/00
[52] U.S. Cl. ................................. 210/800; 210/723; 210/744; 210/767; 210/803
[58] Field of Search .............. 210/702, 767, 708, 723, 210/729, 730, 731, 744, 803, 800, 806, 513, 94, 514, 515, 519; 422/44; 604/4, 404, 407, 416

[56] References Cited

U.S. PATENT DOCUMENTS

| | | | |
|---|---|---|---|
| 2,287,156 | 1/1942 | White | 210/514 |
| 2,436,140 | 2/1948 | Deardorff | 210/514 |
| 3,556,502 | 1/1971 | Rheinlander et al. | 210/800 |
| 3,709,361 | 1/1973 | Miller | 210/94 |
| 4,435,170 | 3/1984 | Laszczower | 604/4 |
| 4,436,634 | 3/1984 | Wells | 210/800 |
| 4,838,855 | 6/1989 | Lynn | 604/4 |

Primary Examiner—Robert A. Dawson
Assistant Examiner—Sun Uk Kim
Attorney, Agent, or Firm—Donald G. Lewis

[57] ABSTRACT

A blood washing device is employed for recovering shed blood or other sources of blood and preparing packed red cells therefrom. The device employs a gravity sedimentation procedure but achieves a shortened washing period by using an aggregating reagent for aggregating or agglomerating the red cells so as to increase their sedimentation velocity during the gravity sedimentation. The wash period is further shortened by employing a vessel with a flat shallow configuration for shortening the sedimentation path length of the aggregated red cells. A non-turbulant removal of the resultant broad shallow layer of sedimented red cells is achieved by carefully tilting the vessel after the sedimentation step so as to induce the sedimented red cells to slide or shift into a funnel configuration within the vessel. After the red cells have shifted into a funnel configuration, they are allowed to stand in that configuration so as undergo further concentration. As the red cells become packed, an elutriation of the intercellular fluids occurs. The resultant packed red cells are then carefully drained from the bottom of the funnel configuration for reinfusion into the patient. The period of the wash cycle is sufficiently short that a patient's shed blood can often be recovered during an operation and then washed and reinfused into the same patient during the same operation or shortly thereafter. Autologous transfusions are useful in cases where there is a shortage of blood or where the safety of donor blood is in question.

3 Claims, 5 Drawing Sheets

BLOOD WASHING METHOD

The invention relates to methods and devices for collecting and washing blood for transfusion. More particularly, the invention relates to autotransfusion devices employed intra-operatively for recovering shed blood and preparing packed red cells therefrom.

BACKGROUND

Autotransfusion systems can often be employed during a surgical procedure to recover and wash shed blood for re-infusion into the patient when donated blood is scarce or unavailable or when there is concern regarding the safety of the donated blood. The autotransfusion system may employ an aspiration system for recovering the shed blood. During the aspiration process, shed blood may be aspirated and directed through a gross clot pre-filter and into a collection vessel. Anticoagulant must be added to the collected blood to prevent clot formation within the collection vessel.

The mixture of collected blood and anticoagulant may be washed by the addition of a wash solution. The wash solution serves to dilute the blood. After dilution with the wash solution, the red cells may be separated from the diluted blood mixture by centrifugation or by gravity sedimentation. During centrifugation and/or gravity sedimentation, the red cells sediment and collect at the bottom of the vessel as packed red cells. The sedimentation of the red cells causes a substantial elutriation of various fluids and particles from packed red cells, including plasma, tissue fluids, anticoagulant, and washing solution. The packed red cells are suspended in residual supernatant. The packed red cell product may then be removed and transferred to a reinfusion bag for reinfusion into the patient from whom it was taken.

Although autotransfusion systems find wide application, their utility is mitigated by the slowness of the gravity sedimentation step and/or the complexity and labor involved with the centrifugation step. What is needed is an autotransfusion system which employs a simple but accelerated gravity sedimentation step for reducing the time delay between collection and reinfusion.

SUMMARY

Definitions:
1. Blood mixture: Whole blood, shed or drawn, or any subfraction of whole blood which includes red cells, with or without additives such as anticoagulants or cryoprotectants.
2. Aggregated red cells: Any reversible aggregate or agglomerate of red cells of the type first described by Charles Huggins {Science 139 (1963), 504-5: incorporated herein by reference}, having a markedly increased sedimentation velocity under gravity sedimentation as compared to unaggregated red cells. Preferred aggregated red cells have as many as 50-150 red cells per aggregate. Hespan (TM-DuPont) is a preferred reagent for aggregating red cells. However, other effective reagents are also known.
3. Sedimented red cells: A collection or assembly of red cells and red cell aggregates which have sedimented from a blood mixture to or adjacent to the bottom of the vessel to form a sedimentation layer.
4. Packed red cells: Sedimented red cells from which the intercellular fluids have further elutriated so as to cause the red cells to become more concentrated or more tightly "packed" with respect to one another.

The invention is an autotransfusion system which employs an accelerated gravity sedimentation step. In a preferred mode, the blood mixture is first aspirated into a reservoir having demarcations for indicating fullness and an automatic shut-off mechanism to prevent overfilling so as to leave room for the addition of reagents and so as to leave room for mixing. Accelerated gravity sedimentation is then achieved, in part, by adding a reagent which aggregates the red cells. In the presence of one such reagent, i.e. an isotonic solution of hetastarch, red cells form aggregates with a size of up to 50-150 cells per aggregate. The large size of such aggregates causes them to a sedimentation velocity which is much greater than that of an individual red cell. After the addition of this reagent, the reagent is then blended with the collected blood by rocking the reservoir. To achieve such blending, it is important to leave room within the reservoir for the fluid therein to undergo a rocking or wave motion so as to blend the reagent with the blood mixture.

Accelerated gravity sedimentation is also achieved by reducing the length of the sedimentation path. For a given volume of blood, the length of the sedimentation path may be reduced by employing a vessel or reservoir having a broad flat bottom. In such a reservoir, the blood mixture forms a shallow pool over a relatively wide area. The path length from the surface of the blood mixture to the bottom of the reservoir is relatively short. Unfortunately, after the sedimentation step is complete, the broad thin layer of sedimented red cells can be difficult to transfer from the reservoir without disturbing the interface between the sedimented red cells and the supernatant and without causing mixing therebetween. Accordingly, efficient transfer of the sedimented red cells is achieved by tilting or reorienting the reservoir from its flat shallow configuration to a second configuration having a funnel configuration. The tilting or reorientation of the reservoir proceeds slowly so that the flat layer of sedimented red cells can slide or shift slowly along the bottom of the flat shallow portion of the reservoir into the funnel configuration of the reservoir without mixing or turbulence. Sliding the sedimented red cells into a funnel configuration facilitates the further packing of such red cells and facilitates the resultant elutriation of further fluids from such packed cells.

After the sedimented red cells are shifted into a funnel configuration and allowed to become more packed, the resultant red cells are then removed from the reservoir by being pumped from an exit port at the bottom of the funnel. The packed red cells are then ready to be reinfused into the patient.

BRIEF DESCRIPTION OF THE DRAWINGS

FIG'S 1 (a-q) are schematic views illustrating the method of the invention.

FIG'S 1 (a-d) illustrate the aspiration of the blood mixture into the reservoir and the addition of the reagent for aggregating red cells.

FIG. 1 (b) illustrates a reservoir oriented in its collection configuration with a blood mixture being aspirated thereinto.

FIG. 1 (c) illustrates the completion of the aspiration of the blood mixture into the reservoir and the activation of the vacuum shut-off which prevents the further aspiration of blood into the reservoir.

FIG. 1 (d) illustrates the addition of the reagent to the reservoir for aggregating red cells.

FIG'S 1 (e-f) illustrate the blending of the blood mixture with the reagent for aggregating red cells within the reservoir by means of a rocking motion. FIG. 1(e) represents an upward movement of the rocking motion; FIG. 1(d) represents a downward movement of the rocking motion. FIG'S 1 (g-i) illustrate the gravity sedimentation of aggregated red cells from the blended blood mixture. FIG. 1 (g) illustrates a reservoir oriented in its flat shallow configuration at the start of the sedimenation process prior to any significant sedimentation. FIG. 1 (h) illustrates a reservoir oriented in its flat shallow configuration at an intermediate stage of the sedimentation process and illustrates the intermediate formation of a flat shallow layer of sedimented red cells.

FIG. 1 (i) illustrates a reservoir oriented in its flat shallow configuration at the final stage of this sedimentation process and illustrates the formation of a substantially complete flat shallow layer of sedimented red cells.

FIG'S 1 (j-m) illustrate the slow reorientation of the reservoir from its flat shallow configuration to its funnel configuration and illustrate the slow shifting of the flat shallow layer of sedimented red cells into the funnel configuration. The reorientation proceeds progressively with FIG'S 1 (j-l) illustrating intermediate configurations and Fig. (m) illustrating the final reorientation into the funnel configuration.

FIG'S 1 (n-o) illustrate the packing of the shifted layer of sedimented red cells within the funnel configuration and the elutriation of fluids therefrom. The extent of packing of the sedimented red cells increases from FIG. 1 (n) to FIG. 1 (o).

FIG'S 1 (p-q) illustrate the draining or pumping of the packed red cells from an exit port at the bottom of the funnel configuration. The removal from the reservoir of the packed red cells is complete in FIG. 1 (q).

Figure 2:
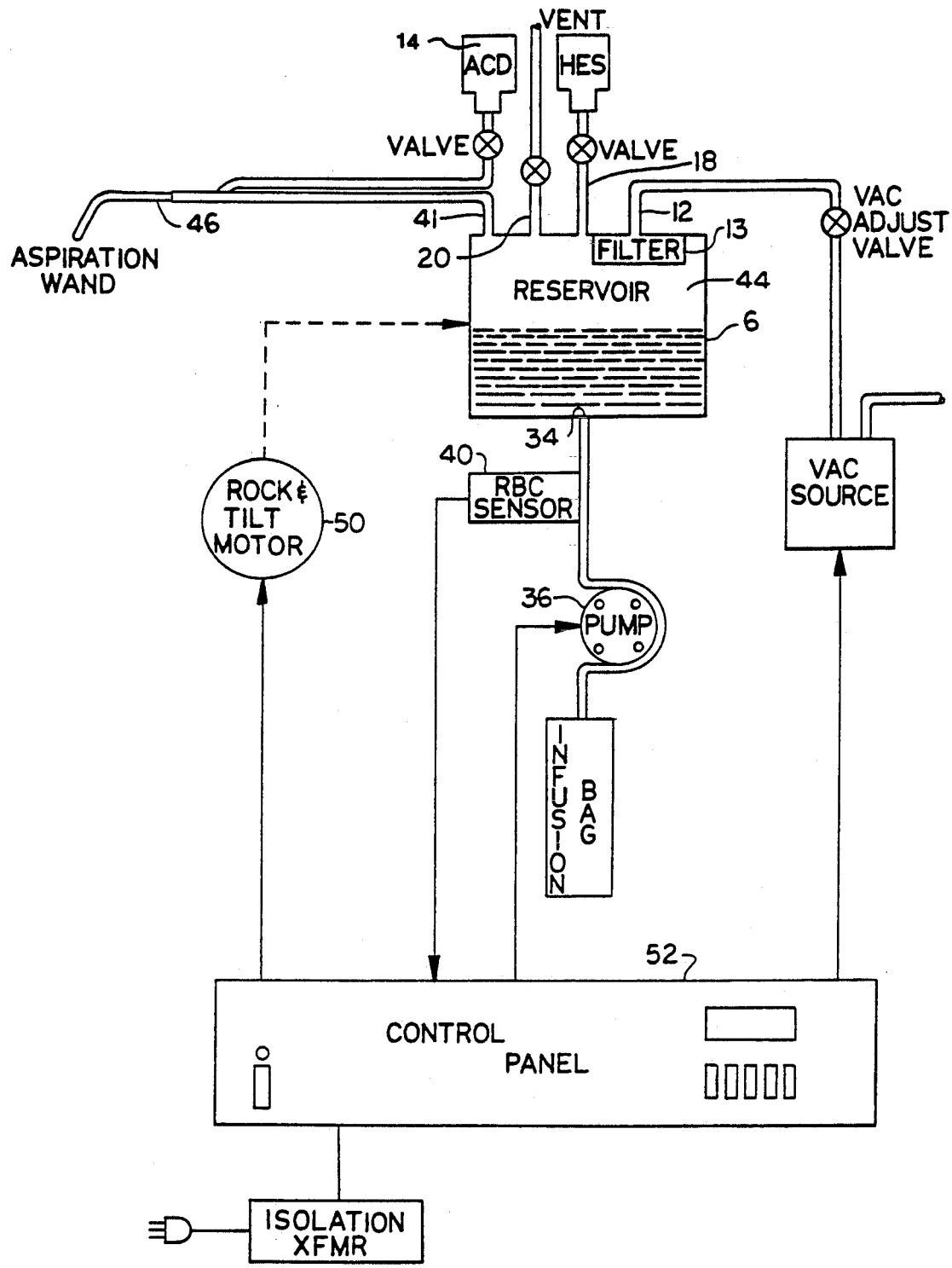

FIG. 2 is a schematic view illustrating an apparatus for aspirating a mixture of shed blood and recovering packed red cells therefrom.

Figure 3:
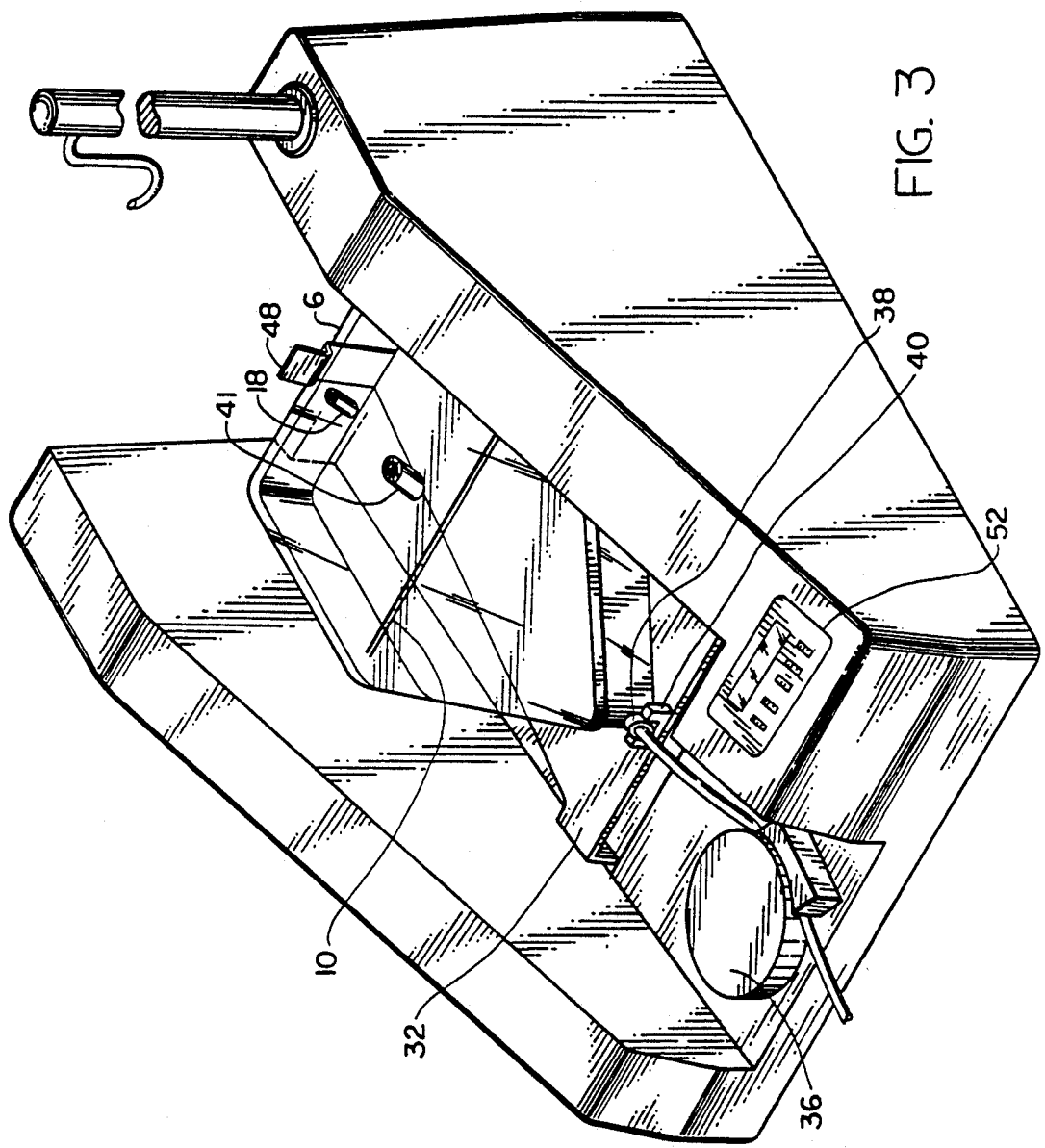

FIG. 3 is a perspective view of a preferred embodiment of an apparatus for preparing packed red cells from a mixture of shed blood, illustrating a reservoir, a tilt platform, and a pump.

Figure 4:
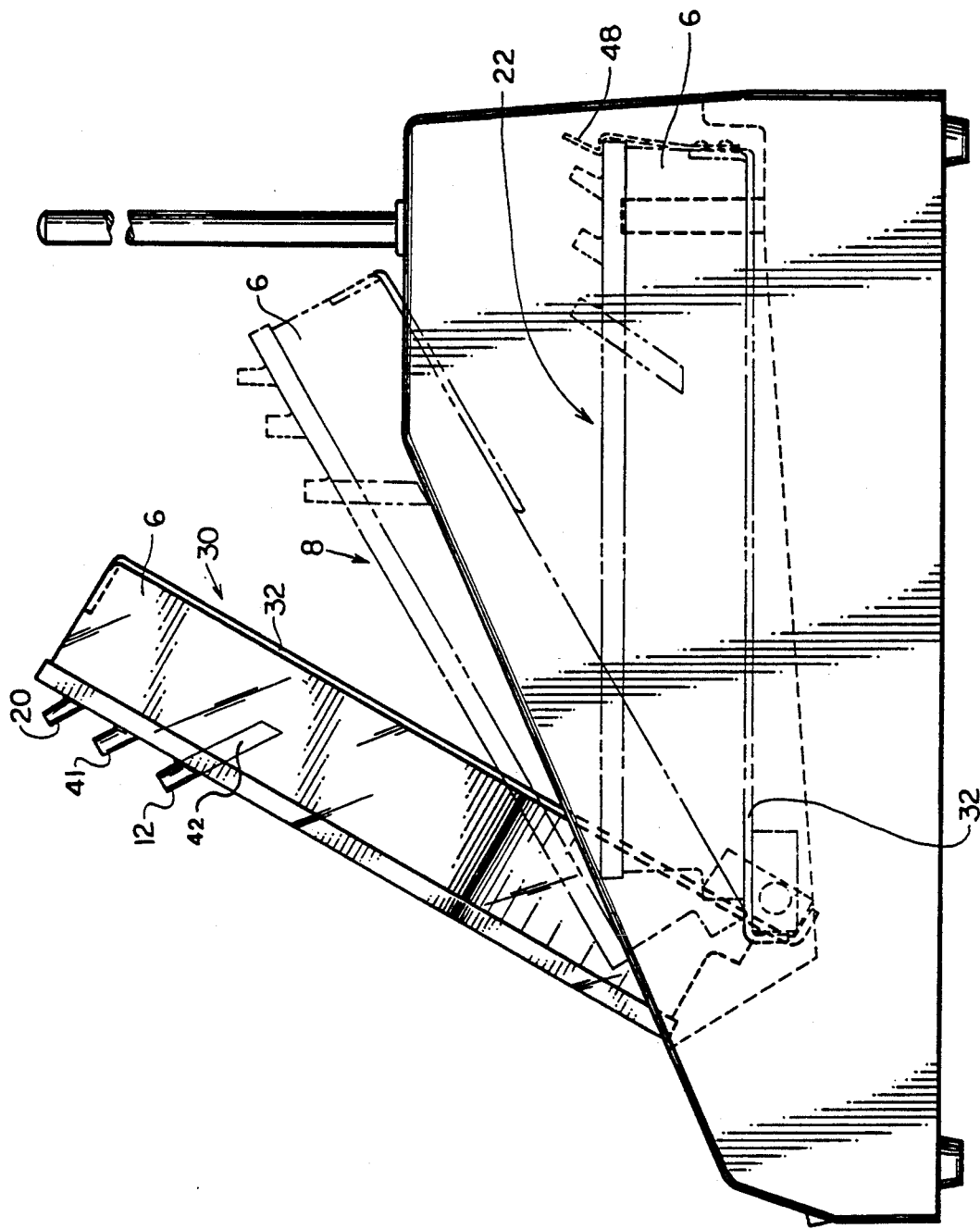

FIG. 4 is a plan view of the side of the apparatus shown in FIG. 3, illustrating the reservoir oriented within its flat shallow configuration, its collection configuration, and its funnel configuration.

Figure 5:
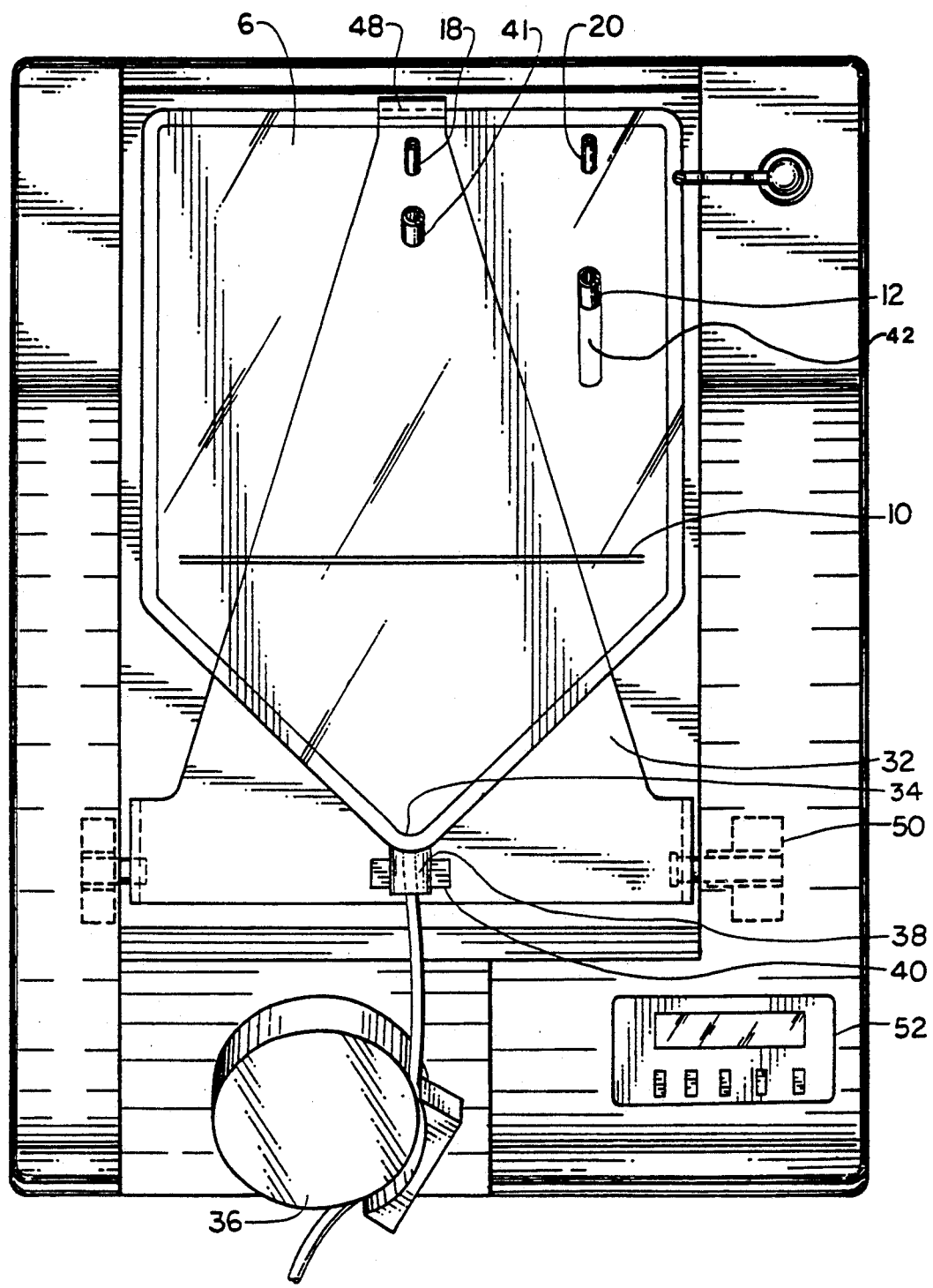

FIG. 5 is a plan view of the top of the apparatus shown in FIG. 3.

DETAILED DESCRIPTION

Method for Recovering a Mixture of Shed Blood and Preparing Packed Red Cells Therefrom A schematic outline of the method is provided in FIG'S 1 (a-q). In the preferred mode, the method is employed for recovering shed blood and preparing packed red cells (2) therefrom. However, the method may also be employed for washing drawn blood, including drawn blood which has been frozen with cryopreservatives, and preparing packed red cells therefrom for transfusion.

Depending upon the source of the blood, the blood or blood mixture (4) is aspirated or otherwise transferred into a special reservoir (6) or vessel. The aspiration of a blood mixture (4) into a reservoir (6) is illustrated in FIG. 1(b). In a preferred mode, the reservoir (6) is oriented within a collection configuration (8) at an angle of 30 degrees with respect to the horizontal during the aspiration process, as illustrated in FIG. 1(b). However, other angles which are also significantly off the horizontal may also be employed with respect to the collection configuration (8). Orienting the reservoir (6) within the collection configuration (8) facilitates the visualization of the relative fullness of the reservoir (6) by the user. For reasons indicated below, the reservoir (6) should not be over filled during the aspiration process. In the preferred mode, the collection configuration (8) of the reservoir (6) has an angle significantly above the horizontal as indicated in FIG. 1(b) so that the rise of the blood level within the reservoir (6) is significantly more noticable as compared to the horizontal. To further facilitate the visualization of the relative fullness of the reservoir (6), one or more demarcations (10) may be placed on the reservoir (6) in a position that may be easily compared to the actual blood level. In an alternative mode, the method may include the use of an automatic shut-off within the vacuum port (12) for terminating the further aspiration of blood when the reservoir (6) has reached its proper level of fullness. In a preferred embodiment, the shut-off is constructed by placing a hydrophobic filter or membrane (13) within the vacuum port (12) of the reservoir (6). When the membrane (13) is dry, it freely passes air. However, when the membrane (13) becomes wet, the passage of liquids is blocked. Hence, when the aspirated blood mixture (4) reaches the level of the vacuum port (12) so as to draw the blood mixture (4) therein, the hydrophobic membrane (13) becomes wet and blocks the further passage of air or liquids therethrough. Alternatively, a floating ball valve arrangement may be employed as the vacuum shut-off.

In the preferred mode, anticoagulant (14) is added to the blood during the aspiration process to prevent clotting. A schematic system for adding acid citrate dextrose (ACD) as an anticoagulant (14) during the aspiration process is illustrated in FIG. 2. The combination of aspirated blood and anticoagulant (14) comprises a preferred form of blood mixture (4) from which packed red cells (2) may be prepared. It can be important to remove the ACD from the aspirated blood prior to reinfusion because excessive infusion of ACD into a patient can cause uncontrolled bleeding.

After the blood is aspirated or otherwise transferred into the reservoir (6), a reagent (16) for aggregating red cells is added to the reservoir (6). The preferred reagent (16) for aggregating red cells is a product called Hespan (TM) or HES, made by DuPont. HES is a 6% solution of hetastarch in 0.9% sodium chloride. A preferred method for adding the reagent (16) to the reservoir (6) is illustrated in FIG. 1(d). A port (18) for adding the HES and a port (20) for venting displaced air from the reservoir (6) are schematically illustrated in FIG. 2.

After the reagent (16) for aggregating red cells is added to the reservoir (6), the blood mixture (4) is blended with the reagent (16) so as to initiate the aggregation process. A preferred mode for blending the blood mixture (4) and the reagent (16) involves rocking the reservoir (6). The process of rocking is illustrated in FIG'S 1(e-f). As seen in the illustration, the rocking method starts to become ineffective for blending the blood with the reagent (16) if the reservoir (6) is significantly more than 95% full.

In a preferred mode, the reservoir (6) has a capacity of 2000 milliliters; 1200 milliliters of blood mixture (4) can be aspirated into the reservoir (6) before the automatic shut-off is activated; and 500 milliliters of reagent (16) are then added via the reagent port (18); leaving an extra 300 milliliters of space within the reservoir (6) for the rocking motion to occur to blend the blood mixture (4) with the reagent (16). It has been found that adequate mixing by the rocking method requires about 2 minutes.

Figure 1:
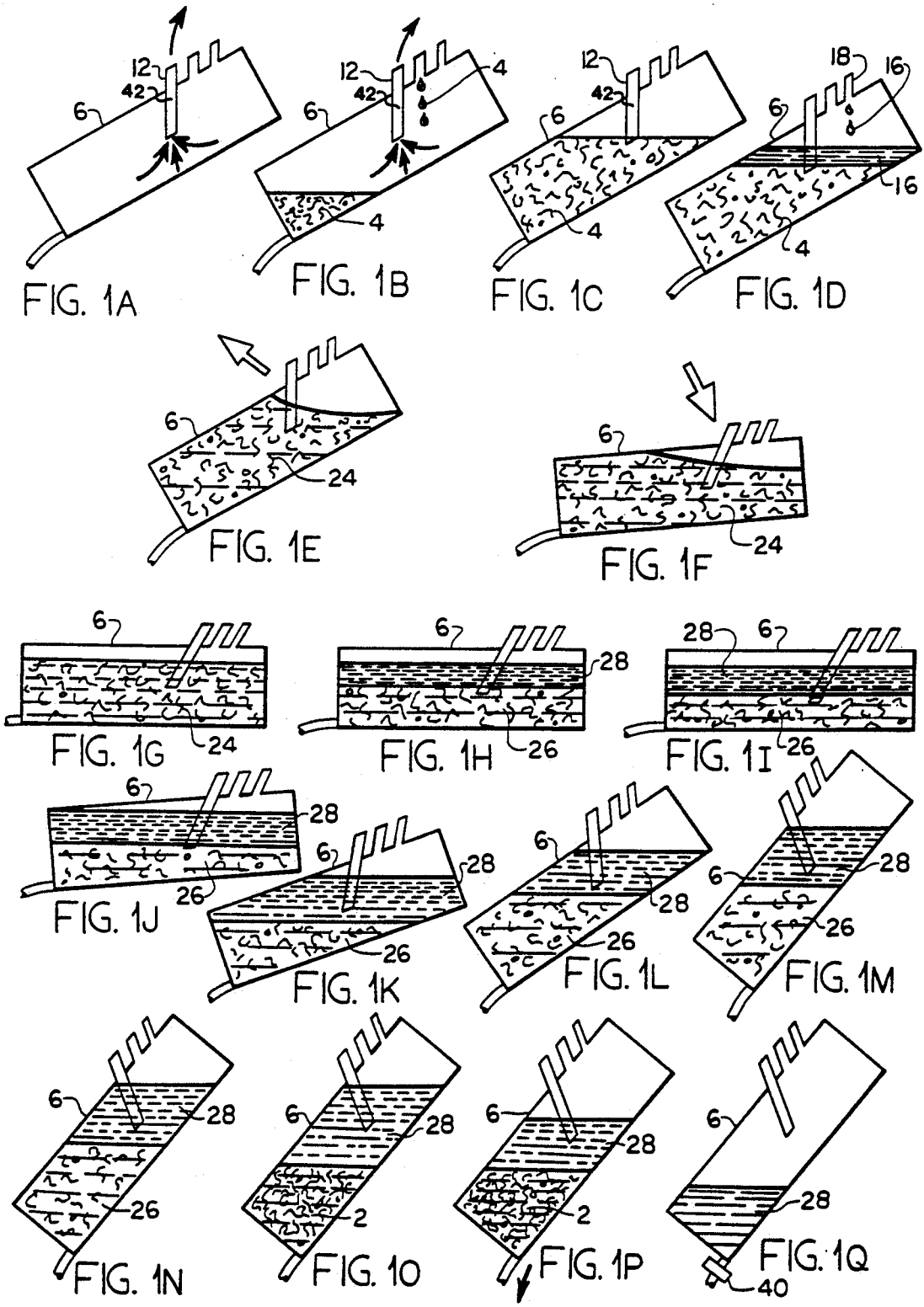
FIG. 1 (a) illustrates an empty reservoir oriented in its collection configuration, evacuated and ready to receive aspirated blood.

After blending the blood mixture (4) with the reagent (16), the reservoir (6) is then reoriented to a flat shallow configuration (22) as illustrated in FIG. 1 (g) in order to accelerate the separation of the aggregated red cells (24) from the blood mixture (4). The flat shallow configuration (22) may also be called the sedimentation position. In the flat shallow configuration (22), the fluid within the reservoir (6) is spread over the widest possible area and the average depth of the fluid within the reservoir (6) is minimized. Also minimized is the average sedimentation path length for the red cell aggregates (24). Hence, orienting the reservoir (6) within the flat shallow configuration (22) shortens the time required for aggregated red cells (24) to sediment from the blended blood mixture (4) into a flat shallow layer of sedimented red cells (26) on the bottom of the reservoir (6). In a preferred embodiment, the reservoir (6) is retained within the flat shallow configuration (22) for 8 minutes so as to allow the aggregated red cells (24) an opportunity to sediment from the blood mixture (4) into a flat shallow layer of sedimented red cells (26). The progressive formation of the flat shallow layer of sedimented red cells (26) is illustrated in FIG'S 1(h-i).

After the gravity sedimentation step is substantially complete, the sedimented red cells (26) need to be removed from the reservoir (6). Removing a broad shallow layer of sedimented red cells (26) from its supernatant (28) without turbulence or mixing can be difficult. Accordingly, in order to circumvent this problem, the reservoir (6) is slowly eased or reoriented from the flat shallow configuration (22) or sedimentation position to a funnel configuration (30). The reorientation may be achieved by tilting the platform (32) to which the reservoir (6) is attached. This reorientation causes the flat shallow layer of sedimented red cells (26) to slowly slide or shift along the bottom of the flat shallow portion of the reservoir (6) into the funnel configuration (30) of the reservoir (6). If the tilting or reorientation is performed slowly and gently, the shift of the shallow layer of sedimented red cells (26) can occur without mixing the sedimented red cells (26) with the supernatant (28) or other turbulence. In a preferred embodiment, the funnel configuration (30) of the reservoir (6) has an angle of 60 degrees with respect to the horizontal. An example of the funnel configuration (30) is illustrated in FIG. 1(m) and in FIG. 4. Sliding the sedimented red cells (26) into a funnel configuration (30) allows the red cells to be drained from the reservoir (6) with a minimum of turbulence.

Sliding the sedimented red cells (26) into a funnel configuration (30) also facilitates the further packing of such red cells and facilitates the resultant elutriation of further fluids from such packed red cells (2). In a preferred embodiment, the reservoir (6) is held or retained in the funnel configuration (30) for 10 minutes in order to allow the red cells to become packed and to concentrate near the exit port (34). An example of the process of red cell concentration or packing is illustrated in FIG'S 1 (n-o).

After the packing process is substantially complete, the packed red cells (2) are ready to be removed from the funnel portion of the reservoir (6). While retaining the reservoir (6) in the funnel configuration (30), a pump (36) is activated which draws the packed red cells (2) from an exit port (34) at the bottom of the funnel. The packed red cells (2) are slowly drawn from the reservoir (6) and transferred to a reinfusion bag for later use. As packed red cells (2) are slowly drawn from the exit port (34), the layer of packed red cells (2) within the funnel portion of the reservoir (6) are drawn down toward the exit port (34). The transfer of the red cells from the funnel portion of the reservoir (6) is illustrated in FIG'S 1(p-q).

Substantially no turbulence occurs until the packed red cells (2) are substantially exhausted from the reservoir (6). As the last red cells are drawn from the reservoir (6) into the exit port (34), supernatant (28) may start to mix with the pack red cells. Once inside the exit port (34), the flow quickly converts from blunt flow to laminar flow. Laminar flow causes mixing to occur. Accordingly, in order to minimize the mixing caused by laminar flow, the exit port (34) of the reservoir (6) may include an optical element (38) which can be coupled to sensor (40) for sensing the passage of packed red cells (2) and supernatant (28). The position of this optical element (38) at the very mouth of the exit port (34) allows the interface of the packed red cells (2) and the supernatant (28) to be detected before any substantial mixing has occurred within the exit port (34) of the line leading therefrom to the reinfusion bag. In the preferred mode, the pump (36) for transferring the packed red cells (2) from the reservoir (6). is inactivated once the sensor (40) attached to the optical element (38) or path on the exit port (34) of the reservoir (6) detects the interface between the packed red cells (2) and the supernatant (28).

The Reservoir

A preferred embodiment of the reservoir (6) is illustrated in FIG'S 3–5. The reservoir (6) is attachable to an apparatus for processing the blood mixture (4). All of the processing which occurs to the blood mixture (4) occurs within the reservoir (6). The reservoir (6) serves as a collection vessel for the blood. The reservoir (6) also serves as the vessel in which the blood mixture (4) is diluted with reagent (16) and in which the red cells therein are sedimented and packed and from which the resultant packed red cells (2) are removed.

In the preferred embodiment, the reservoir (6) includes three configurations, viz. a collection configuration (8), a flat shallow configuration (22), and a funnel configuration (30). All three configurations are illustrated in FIG. 4. The reservoir is oriented into each of these configurations in succession so as to perform the particular function for which the configuration is designed.

Initially, the reservoir (6) is oriented within the collection configuration (8) for collecting the blood mixture (4). In the preferred mode, when the reservoir (6) is oriented within the collection configuration (8), the bottom of the reservoir (6) and the platform (32) upon which it is supported is oriented at an angle of approximately 30 degrees with respect to the horizontal, as illustrated in FIG'S 1(a-c) and FIG. 4. As compared to the horizontal position, the user can more easily visualize the fullness of the reservoir (6) when the reservoir is oriented with this 30 degree angle. It is important for the physician or health care provider not to overfill the reservoir (6) with the blood mixture (4) during the collection process. In a preferred embodiment, the optimal quantity of blood mixture to collect into the reservoir (6) lies between one half and three quarters of the volume of the reservoir (6). The reservoir (6) may be transparent and may include one or more demarcations (10) for visualizing the fullness of the reservoir (6) during this collection process. As compared to the horizontal position, the 30 degree angle of the collection configuration (8) imparts a greater sensitivity to these demarcations (10) for visualize the level of the blood mixture (4) within the chamber (44).

In the preferred mode, the blood mixture (4) is collected by aspiration into the reservoir (6) into an aspiration port (41). The reservoir (6) includes a chamber (44) into which the blood mixture (4) is aspirated or otherwise collected. If aspiration is employed to collect the blood mixture (4), then the reservoir (6) must be sufficiently rigid and must have sufficient strength to contain a vacuum. The reservoir (6) must also include a vacuum port (12) for evacuating the chamber (44) and an aspiration or collection port for admitting the aspirated blood mixture (4).

Overfill can be avoided by employing an automatic shut-off mechanism within the vacuum port (12). In the preferred embodiment, the automatic shut-off is incorporated into the vacuum port (12). When the automatic shut-off is activated, the vacuum source is closed and the aspiration of further blood mixture (4) ceases. In the preferred mode, a vacuum shut-off is incorporated into a vacuum port (12) so as to shut off the vacuum when the designated level of fullness is achieved. The vacuum shut-off is activated when the blood mixture (4) starts to be drawn into the vacuum port (12) or the vacuum port (12) otherwise starts to become submerged.

The fluid level at which the vacuum shut-off is activated can be controlled by the placement of the inlet to the vacuum port (12). In a preferred embodiment, the vacuum port (12) includes an extension (42) protruding into the interior of the chamber (44). The inlet of the vacuum port (12) is located at the end of this extension (42). The extension (42) is then positioned within the chamber (44) so as to become submerged within the blood mixture (4) whenever the chamber (44) reaches a desired level of fullness.

In the preferred mode, the fluid level at which activation of the vacuum shut-off occurs is relatively independent of the orientation of the reservoir (6) with respect to the collection configuration (8), the flat shallow configuration (22), the funnel configuration (30), and intermediate configurations therebetween. If the inlet of the extension (42) of the vacuum port (12) is positioned within the interior of the chamber (44) as indicated in FIG'S 1(a-q) and FIG'S 4-5, the fluid level at which the vacuum shut-off is activated changes very little as the orientation of the reservoir (6) is changed from one configuration to the next.

After the blood mixture (4) has been collected into the reservoir (6), a reagent (16) for aggregating the red cells is then added to the reservoir (6). In the preferred embodiment, the reagent (16) is added via a loading or reagent port (18). The loading port (18) is incorporated into the reservoir (6) and its outlet within the reservoir (6) may lie above the fill level for the collected blood mixture (4) when the reservoir (6) is oriented within the collection configuration (8).

A ventilation port (20) may also be employed in conjunction with the loading of reagent (16) for venting air to and from the chamber (44) as it is displaced by the addition of the reagent (16) or the subsequent removal of material from the chamber (44) of the reservoir (6).

After the reagent (16) is blended into the blood mixture (4) by means of a rocking process, the reservoir (6) is then reoriented into the flat shallow configuration (22), as illustrated in FIG. 1(g-i) and FIG'S 3-5. In the flat shallow configuration (22), the reservoir (6) is employable for reducing the time required for aggregated red cells (24) to sediment from the blood mixture (4) into a flat shallow layer of sedimented red cells (26). In the flat shallow configuration (22), the collected blood covers the broad flat bottom of the configuration (22) and reduces the sedimentation path length for an aggregate of red cells sediments from the surface of the blood mixture (4) to the bottom of the reservoir (6).

After the completion of the gravity sedimentation step, the reservoir (6) is slowly reoriented to the funnel configuration (30). In a preferred embodiment, the funnel configuration (30) is tilted at a 60 degree angle with respect to the horizontal as illustrated in FIG'S 1(m-q) and FIG. 4. The funnel configuration (30) of the reservoir (6) is characterized by the slanting bottom which leads to and focuses upon the exit or outlet port (34) when the reservoir (6) is oriented in the funnel configuration (30), the exit port (34) is positioned at the lowest point within the chamber (44). When the reservoir (6) is oriented in the funnel configuration (30), the flat shallow layer of sedimented red cells (26) slides or shifts down the slanting bottom toward the exit or outlet port (34) and into the funnel configuration (30) of the reservoir (6). The sedimented red cells (26) become packed when allowed to sit in this position. The packed red cells (2) may be drained by pumping or gravitational flow from the exit port (34) when the reservoir (6) is oriented within the funnel configuration (30).

The reservoir (6) may also include an optical coupler or optical path (38) for coupling to a sensor (40) for sensing red cells as they are removed or pumped from the reservoir (6). In the preferred mode, the optical coupler or optical path (38) is incorporated into the exit or outlet port (34). Positioning the sensor (40) at the mouth of the exit or outlet port (34) provides the earliest possible indication that the chamber (44) has been exhausted of packed red cells (2).

The Apparatus

A preferred embodiment of the apparatus or device for aspirating a mixture of shed blood and for preparing packed red cells (2) therefrom is illustrated in FIG'S 3-5. A schematic view of the same apparatus is illustrated in FIG. 2. The apparatus serves to aspirate shed blood by means of an aspiration wand (46). As shed blood is drawn into the aspiration wand (46), a source of acid citrate dextrose (ACD) or other anticoagulant (14) is activated so as to release anticoagulant (14) into the blood as it is aspirated. The aspirated blood mixture (4) is then drawn into the reservoir (6). In the preferred mode, the reservoir (6) is maintained in a collection configuration (8) during this process of aspirating blood into the reservoir (6).

The apparatus includes a tiltable platform (32) to which the reservoir (6) may be attached by a brace (48)

or other attaching means. The tiltable platform (32) serves to support the reservoir (6) in various configurations. FIG. 4 illustrates the tiltable platform (32) supporting the reservoir (6) within its three configurations, i.e. the collection configuration (8), the flat shallow configuration (22), and the funnel configuration (30).

The apparatus also includes a drive (50) for tilting said platform (32). The drive (50) is capable of driving the tilting platform (32) in a rocking motion and for slowly reorienting the tilting platform (32) from the flat shallow configuration (22) to the funnel configuration (30). The drive (50) is also capable of holding or retaining the platform (32) in each of its three configurations.

The apparatus also includes an automatic processing unit or controller (52) for automating and controlling the drive (50). The controller includes a microprocessor that is connected to the drive (50) and is programed to control the drive (50) so as to perform a drive sequence.

In the preferred mode, the drive sequence commences when the controller (52) directs the drive (50) to position and retain the platform (32) so as to orient the reservoir (6) attached thereto in the collection configuration (8).

After the collection process is complete and the HES reagent (16) or its equivalent has been added to the collected blood, the drive sequence continues when the controller (52) directs the drive (50) to rock the platform (32) so as to cause the collected blood mixture (4) to blend with the added reagent (16) for aggregating the red cells. In the preferred mode, the platform (32) rocks between the collection and the flat shallow configurations (22) during the rocking process.

After the rocking process, the drive sequence continues by directing the drive (50) to position and retain the platform (32) so as to orient the reservoir (6) attached thereto in the flat shallow configuration (22). This serves to reduce the time required for the aggregated red cells (24) to sediment from the collected blood mixture (4) into a flat shallow layer of sedimented red cells (26). In the preferred mode, the flat shallow configuration (22) is retained for about 8 minutes to complete the sedimentation process.

After the sedimentation process is complete, the drive sequence continues by directing the drive (50) to slowly reposition the platform (32) so as to reorient the reservoir (6) thereon from the flat shallow configuration to the funnel configuration (30). This serves to slowly shift the flat shallow layer of sedimented red cells (26) into the funnel configuration (30) of the reservoir (6) without mixing therein.

After the shift to the funnel configuration (30) is complete, the drive sequence continues by directing the drive (50) to stop the platform (32) so as to retain the reservoir (6) attached thereto within the funnel configuration (30). This serves to allow the red cells within the funnel configuration (30) of the reservoir (6) to concentrate therein so as to form packed red cells (2). The process of concentrating or packing red cells takes about 10 minutes.

In a preferred configuration, the microprocessor of the controller (52) is also connected to a sensor (40) and to a pump (36). The controller (52) then serves to perform a pump sequence.

After the process of concentrating or packing the red cells is complete, the pump sequence begins by directing the pump (36) to pump the packed red cells (2) from the funnel configuration (30) of the reservoir (6). During this pumping process, the platform (32) retains the reservoir (6) within the funnel configuration (30) so that the packed red cells (2) can continue to slide or shift to the exit port (34) of the reservoir (6).

In a preferred mode, the apparatus includes a sensor (40) which is coupled to an optical path (38) incorporated into the exit port (34) of the reservoir (6). The sensor (40) is connected to the controller (52) and serves to alert the controller (52) when the transfer of the packed red cells (2) from the reservoir (6) is complete. The pump sequence continues when the sensor (40) signals to the controller (52) that the transfer of packed red cells (2) from the reservoir (6) is complete. At the point that the sensor (40) no longer senses packed red cells (2) from the reservoir (6), the pump sequence continues and terminates by directing the pump (36) to stop the pumping of the packed red cells (2) from the funnel configuration (30) of the reservoir (6). This serves to terminate the sequence.

What is claimed is:

1. A method for recovering a blood mixture and preparing packed red cells therefrom, the method comprising the following steps:

Step A: transferring the blood mixture into a reservoir;

Step B: loading a reagent into the reservoir for aggregating red cells; then

Step C: blending the blood mixture with the reagent for aggregating red cells within the reservoir; then Step D: separating the aggregated red cells from the blended blood mixture by gravity sedimentation in an accelerated fashion by orienting the reservoir into a flat shallow configuration and allowing the aggregated red cells to sediment from the blended blood mixture into a flat shallow layer of sedimented red cells; then Step E: slowly shifting the flat shallow layer of sedimented red cells to a funnel configuration without mixing by slowly reorienting the reservoir from the flat shallow configuration to the funnel configuration; then Step F: packing the shifted sedimented red cells within the funnel configuration by retaining the reservoir in the funnel configuration for allowing the sedimented red cells to become packed therein; then Step G: removing the packed red cells from the blended blood mixture while continuing to retain the reservoir in the funnel configuration by pumping the packed red cells from an exit port at the bottom of the funnel configuration of the reservoir.

2. A method for recovering a blood mixture and preparing packed red cells therefrom, as described in claim 1, wherein:

in said Step A, the reservoir being oriented within a collecting configuration for visualing the fullness of the reservoir by means of one or more demarcations thereon as the blood mixture is collected into the reservoir.

3. A method for recovering a blood mixture and preparing packed red cells therefrom, the method comprising the following steps:

Step A: aspirating the blood mixture into a reservoir attached to a blood washing device;

Step B: adding a reagent for aggregating red cells into the reservoir; then

Step C: blending the blood mixture with the reagent for aggregating red cells by rocking the reservoir on the blood washing device; then Step D: accelerating the separation of the aggregated red cells from the blood mixture by gravity sedimentation employing the blood washing device to reorient the reservoir in a sedimentation position and retaining the reservoir thereat until the red cells have had an opportunity to sediment from the blood mixture into a flat shallow layer of sedimented red cells; then Step E: slowly easing the reservoir from the sedimentation position to a funnel position by means of the blood washing device for slowly shifting the flat shallow layer of sedimented red cells into a funnel configuration without mixing the sedimented red cells with the blood mixture; then Step F: holding the reservoir within the funnel position for allowing the red cells to become packed therein; then Step G: removing the packed red cells from the reservoir while the blood washing device retains the reservoir in the funnel position; and then Step H: stopping the further removal of material from the reservoir after a sensor senses that the reservoir has been substantially exhausted of packed red cells.

* * * * *